(12) United States Patent
Cornelli et al.

(10) Patent No.: US 6,979,680 B1
(45) Date of Patent: Dec. 27, 2005

(54) GLYCOSAMINOGLYCANS HAVING AN AVERAGE MOLECULAR WEIGHT OF 2400 D SUITABLE FOR THE TREATMENT OF SENILE DEMENTIA

(75) Inventors: Umberto Cornelli, c/o Cornelli Consulting S.a.s., Corso Indipendenza 1, 20129 Milano (IT); Luigi De Ambrosi, Santhia' (IT); Israel Hanin, Chicago, IL (US); Jawed Fareed, Westchester, IL (US); John Lee, Wilmette, IL (US); Stanley Lorens, Forest Park, IL (US); Ronald F. Mervis, Columbus, OH (US)

(73) Assignee: Umberto Cornelli, Milan (IT)

( * ) Notice: Subject to any disclaimer, the term of this patent is extended or adjusted under 35 U.S.C. 154(b) by 0 days.

(21) Appl. No.: 10/048,542

(22) PCT Filed: May 12, 2000

(86) PCT No.: PCT/EP00/04311

§ 371 (c)(1),
(2), (4) Date: Apr. 5, 2002

(87) PCT Pub. No.: WO00/69444

PCT Pub. Date: Nov. 23, 2000

(30) Foreign Application Priority Data

May 14, 1999 (IT) .............................. MI99A1066

(51) Int. Cl.[7] ............................................. A01N 43/04
(52) U.S. Cl. ......................................... 514/56; 514/54
(58) Field of Search ........................................ 514/56

(56) References Cited

U.S. PATENT DOCUMENTS

| 4,351,938 A | * | 9/1982 | Barnett et al. | |
| 4,847,338 A | * | 7/1989 | Linhardt et al. | |
| 4,987,222 A | * | 1/1991 | De Ambrosi et al. | ......... 536/21 |
| 5,084,564 A | * | 1/1992 | Vila et al. | ..................... 536/21 |

FOREIGN PATENT DOCUMENTS

| EP | 0 293 974 A1 | 12/1988 | | |
| EP | 0 450 508 A2 | 10/1991 | | |
| IT | 0 450 508 A2 | * 10/1991 | .......... | A61K 31/73 |

OTHER PUBLICATIONS

Snow et al. "An Important Role of Heparan Sulfate Proteoglycan (Perlecan) in a Model System for the Deposition and Persistence of Fibrillar Aβ-Amyloid in Rat Brain" Neuron, vol. 12 pp. 219-234 (Jan. 1994).

George Perry et al., "Association of Heparan Sulfate Proteoglycan with the Neurofibrillary Tangles of Alzheimer's Disease", The Journal of Neuroscience, vol. 11, pp. 3679-3683, Nov. 1991.
D.R. Hinton et al, "Optic Nerve Degeneration In Alzheimer's Disease", J. Neuropathol. Exp Neurol, vol. 45, p. 340, May 1986.
R.N. Kalaria et al., "Acetylcholinesterase And Its Association With Heparan Sulphate Proteoglycans In Cortical Amyloid Deposits of Alzheimer's Disease", Neuroscience, vol. 51, No. 1 pp. 177-184, 1992.
Stanley A. Lorens, Ph.D. et al., "Behavioral, Endocrine, and Neurochemical Effects of Sulfomucopolysaccharide Treatment in the Aged Fischer 344 Male Rat", Seminars in Thrombosis and Hemostasis, vol. 17, Supplement 2, pp. 164-173, 1991.
Luciano Conti et al., "Alteroid In The Treatment of Dementia: Results of a Clinical Trial", Mod Probl Pharmacopsychiatry, vol. 23, pp. 76-84, 1989.
Einar M. Sigurdsson et al., "Local and Distant Histopathological Effects of Unilateral Amyloid- 25-35 Injections Into the Amygdala of Young F344 Rats", Neurobiology of Aging, vol. 17, No. 6, pp. 893-901, 1996.
Bruce A. Yankner et al., Neurotrophic and Neurotoxic Effects of Amyloid Protein: Reversal by Tachykinin Neuropeptides, , Science, vol. 250, pp. 279-250, Oct. 1990.
Lucilla Pametti et al., "Glycosaminoglycan Polysulfate in Primary Degenerative Dementia", Pilot Study if Biologic and Clinical Effects, , Neuropsychobiology, vol. 31, pp. 76-80, 1995.
J.A. Doebler et al., "Hippocampal Neuronal RNA in Alzheimer's Disease", J. Neuropathol Exp Neurol, vol. 45, p. 340, May 1986.
J.P. Willmer et al., "The Demonstration of Sulfated Glycosaminoglycans (GAGs) In Association With The Amyloidotic Lesions of Alzheimer's Diseases", J. Neuropathol Exp Neurol, vol. 45, p. 340, May 1986.

* cited by examiner

Primary Examiner—James O. Wilson
Assistant Examiner—Traviss C. McIntosh, III
(74) Attorney, Agent, or Firm—Morgan & Finnegan, L.L.P.

(57) ABSTRACT

The present invention relates to the use of glycosaminoglycans having an average/molecular weight of 2,400 D for the preparation of pharmaceutical compositions suitable for the treatment of senile dementia, in particular for the treatment of Alzheimer's disease or SDAT (Senile Dementia Alzheimer's Type) and of the cerebral neurological lesions from ictus and from traumas.

6 Claims, 2 Drawing Sheets

| | | | |
|---|---|---|---|
| 16.127 | 0. | 5866.26 | 0. | 0. |
| 16.297 | 0. | 5428.09 | 0. | 0. |
| 16.667 | 0. | 5027.01 | 0. | 0. |
| 16.927 | 0. | 4671.71 | 0. | 0. |
| 17.197 | 4830. | 4331.18 | 0.826 | 0.026 |
| 17.467 | 43261. | 4016.38 | 0.235 | 0.262 |
| 17.727 | 223780. | 3734.94 | 1.218 | 1.48 |
| 17.997 | 791506. | 3462.87 | 4.308 | 5.788 |
| 18.267 | 1798407. | 3209.29 | 9.788 | 15.576 |
| 18.527 | 2903923. | 2980.92 | 15.805 | 31.381 |
| 18.797 | 3625115. | 2756.68 | 19.731 | 51.112 |
| 19.067 | 3635777. | 2550.34 | 19.789 | 70.901 |
| 19.327 | 2791703. | 2361.78 | 15.195 | 86.096 |
| 19.597 | 1559395. | 2177.55 | 8.487 | 94.583 |
| 19.867 | 624025. | 2084.31 | 3.396 | 97.979 |
| 20.127 | 209267. | 1847.21 | 1.139 | 99.118 |
| 20.397 | 79113. | 1693.56 | 0.431 | 99.549 |
| 20.667 | 43730. | 1549.09 | 0.238 | 99.787 |
| 20.927 | 24460. | 1418.23 | 0.133 | 99.92 |
| 21.197 | 14663. | 1290.52 | 0.00 | 100. |
| TOTALS | 18372955. | 0.4935↑+11 | | |

Wt. Avs MWt = 2686       No. Avs MWt = 2624
Z Avs MWt = 2746         Z+1 Avs MWt = 2806
Polydisp. Index = 1.0235772    Visc.Avs = 2686
Fit Type (FT) = 3        Intrinsic Visc. = 0.

GLYCOSAMINOGLYCANS HAVING AN AVERAGE MOLECULAR WEIGHT OF 2400 D SUITABLE FOR THE TREATMENT OF SENILE DEMENTIA

FIELD OF THE INVENTION

The present invention refers to glycosaminoglycans having a low molecular weight, suitable for the treatment of senile dementia and of the cerebral neurological lesions from ictus and from traumas.

PRIOR ART

Senile dementia, particularly in the form of Alzheimer, is principally characterized by cerebral deposits of amyloid substance in plaques, either in the cerebral vessels (vascular amyloid) or in the cerebral substance (cerebral amyloid), both defined as β amyloid or Aβ. The other typical characteristic of senile dementia on the physiopathologic level is the presence in the neurons of fibrillary tangles called NFT (neurofibrillary tangles).

It is known that the proteoglycans (PGs), and in particular the heparan sulfate proteoglycans (HSPG) are involved either in the polymerization of the Aβ or in the aggregation of the NFTs as well as also in other pathologic events related to the Alzheimer's disease and generally to senile dementia (Snow A D; Sekiguchi R; Nicholin D et al. "An Important Role of Heparan Sulfate Proteoglycan (Perlakan) in a Model System for the Deposition and Persistance of Fibrillar Beta Amyloid in Rat Brain." Neuron 1994; 12: 219–234) and (Perry G; Sieslak S L; Richey P; Kawai M et al. "Association of Heparan Sulfate Proteoglycan with Neurofibrillary Tangles of Alzheimer's Disease." J. Neurosci. 1991; 11: 3679–3683).

Moreover the original paper by Snow (Willmer J P; Snow A D; Kisilevski R. "The Demonstration of Sulfate Glycosaminoglycans in Association with the Amyloidogenic Lesions in Alzheimer's Disease". J. Neuropath. Exp. Neurol. 1986; 45: 340–346) discloses the presence of Pgs and of glycosaminoglycans (GAGs) in the cerebral amyloid plaques of patients suffering from senile dementia.

Several studies showed (Kalaria R N; Kroon S N; Grahovak I; Perry G. "Acetylcholinesterase and its Association with Heparan Sulfate Proteoglycans in Cortical Amyloid Deposits of Alzheimer's Disease". Neuroscience 1992; 51:177–184) that the association between PGs and amyloid may be caused either by a direct linkage with the precursor of the β amyloid (AβPP) or by a linkage with Aβ1–41 or with Aβ1–43 which include the neurotoxic sequences of the Aβ.

The Pgs proved to increase also the polymerization of the Tau-2 protein (Perry G; Sieslak S L; Richey P, Kawai M et al. "Association of Heparan Sulfate Proteoglycan with Neurofibrillary Tangles of Alzheimer's Disease". J. Neurosci. 1991; 11: 3679–3683) which is the cause of the formation of the neurofibrillary tangles (NFT).

Moreover in a study carried out by Lorens et al. (Lorens S A; Gushawan B S; Van De Kar L; Walegnga J M; Fareed J. "Behavioural, Endocrine, and Neurochemical Effects of Sulfomucopolysaccharide Treatment in the Aged Fischer 344 Male Rat". Semin Thromb. Haemost. 17 Suppl. 1993; 2:164–173) aged rats showed an improvement of the behavioural deficit following the oral administration of glycosaminoglycans having a high molecular weight (GAP or glycosaminoglycans polysulfated or Ateroid®).

Conti et al. (Conti L; Placidi G F; Cassano G B; "Ateroid® in the Treatment of Dementia: Results of a Clinical Trial (Eds. Ban E; Lehmann H E) Diagnosis and Treatment of Old Age Dementias" Mod. Probl. Pharmacopsychiatry. Basel, Larger 1989 vol. 2, pp 76–84) showed that following the treatment with Ateroid® the patients suffering from senile dementia show an improvement of the psychopathologic parameters performance and of the social behaviour in a significantly higher way than the patients treated with placebo.

Parnetti et al. (Parnetti; Ban T A; Senin U. "Glycosaminoglycan Polysulfate in Primary Degenerative Dementia". Neuropsychobiology 1995; 31: 76–80) showed that Ateroid® may significantly improve some biochemical parameters altered in senile dementia, such as for example the monoamine oxidase B of the blood plaques and the dopamine and serotonin levels in the cerebrospinal fluid.

These observations suggest that Ateroid® may be helpful in the treatment of senile dementia and already in 1988 U. Cornelli and T. Bann obtained the patent for the use of this product in the treatment of senile dementia (EP 293974).

SUMMARY

Now we have surprisingly found in an in vivo experimentation that the fraction of glycosaminoglycans obtained from heparin depolymerization, having an average molecular weight of 2,400 D shows an exceptional effectiveness in inhibiting the formation of the β amyloid and in favouring the neuronal growth.

The fractions having a lower (640 D) average molecular weight or high (4800 D) molecular weight show a definitely lower or negligible effectiveness.

Therefore the fraction of glycosaminoglycans having an average molecular weight equal to 2,400 D may be used for the preparation of pharmaceutical compositions suitable for the treatment of senile dementia, in particular for the treatment of Alzheimer's disease or SDAT (Senile Dementia Alzheimer's Type), and in the treatment of the cerebral neurological lesions from ictus and from traumas.

DETAILED DESCRIPTION OF THE INVENTION

Figure 1:
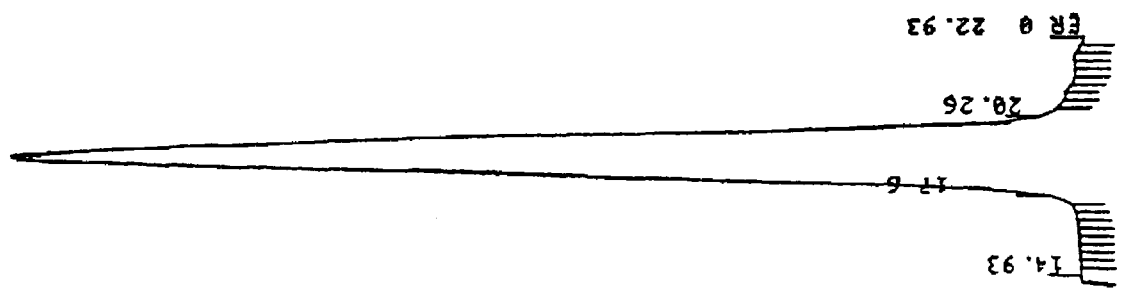
FIG. 1 represents the HPLC test of the glycosaminoglycan having an average molecular weight of 2,400 (±200) as obtained by the described example.

The present invention refers to the use of a fraction of glycosaminoglycans having an average molecular weight of 2,400 D for the preparation of pharmaceutical compositions suitable for the treatment of senile dementia, in particular for the treatment of Alzheimer's disease or SDAT (Senile Dementa Alzheimer's Type) and of the cerebral neurological lesions from ictus and from traumas.

The fraction of glycosaminoglycans is obtained by depolymerization of heparin preferably acting according to a method including the following steps:

a) an aqueous solution of heparin is treated with gamma radiation from Co 60 according to U.S. Pat. No. 4,987,222;

b) the solution obtained from step a) is fractioned by gel permeation on Sephadex G/50 Medium resin;
c) the mixture of the fractions having a molecular weight from 1,000 to 3,000 D is ultrafiltered at 600 D cut-off, washed and freeze-dried;
d) the freeze-dried product is dissolved and fractioned by gel permeation on Sephadex G/25 Medium resin;
e) the fractions having a molecular weight ranging from 1.920 to 2,560 D, corresponding to an average molecular weight equal to 2,400 D, are gathered and mixed.

For the preparation of the fraction of glycosaminoglycans having an average molecular weight equal to 2,400 D, with the preferred method of the present invention, a 10% heparin aqueous solution is first treated with gamma radiation from Co 60 with an intensity ranging from 120 KGy to 150 KGy, at subsequent dosages of 25 KGy with respect to the heparin molecular weight.

The irradiated solution is ultrafiltered at 300 D cut-off, purified, sterilely filtered and freeze-dried obtaining the "mother depolymerized" heparin.

This "mother depolymerized" heparin is dissolved in a 0.3 M solution of NaCl and then submitted to fractioning by gel permeation on Sephadex G/50 Medium resin. The fractions having molecular weight <3,000 D (about 10% of the total) form the raw material of the present invention.

The first treatment of this mixture consists in the ultrafiltration at 600 D cut-off for the removal of the molecular fragments resulting from the depolymerization process.

The ultrafiltered mixture is washed with 0.3 M NaCl to the disappearance of the reaction to carbazole in the permeate.

The final mixture, taken to a concentration about equal to 8% in distilled water, is sterilely filtered on 0.2μ membranes and freeze-dried.

The freeze-dried product is dissolved in a 0.3 M NaCl solution at a concentration ranging from 10% to 15% (w/v).

In order to obtain the fraction having average molecular weight equal to 2,400 D a second treatment of gel permeation is applied maintaining about the same parameters of the first gel permeation, using however the specific characteristics of the Sephadex G/25 Medium.

The used pilot column may be of the BP 252/15 kind with the following characteristics:

| | |
|---|---|
| Height: | 105 cm |
| Resin volume: | 5,200 ml |
| Flux | 1,000 ml/h |
| The adopted parameters are represented by: | |
| Ve = | 17,000 ml |
| Ve/Vo = | 1/R = 1.26 |
| R = | 0.79 |
| K = | 0.09 = (Ve − Vo):(Vt − Vo) | wherein:
Ve = elution volume
Vt = total volume of the resin
Vo = dead volume (initial solution in output)
R = resolution (peak amplitude)

From the second gel permeation from 10 to 12 fractions are obtained comprising a series of molecular weights ranging from 3,000 D to about 1,500 D. For the preparation of the fraction of glycosaminoglycans according to the present invention only the fractions having molecular weights ranging from 1,920 D to 2,560 D are gathered and mixed.

The resulting solution is ultrafiltered by cut-off 300 to the removal of the sodium chloride.

The solution is submitted to concentration to about 10%, filtered at 0.2μ and freeze-dried.

This fraction forms about 80% of the total of the fractions having molecular weight <3,000 D.

According to the method of the present invention the desired fraction of glycosaminoglycans is obtained with noteworthy reproducibility index either as far as the process yield is concerned or as far as the constancy of the molecular composition is concerned.

Below the characterization of the fraction of the glycosaminoglycans of the present invention is reported.

Figure 2:
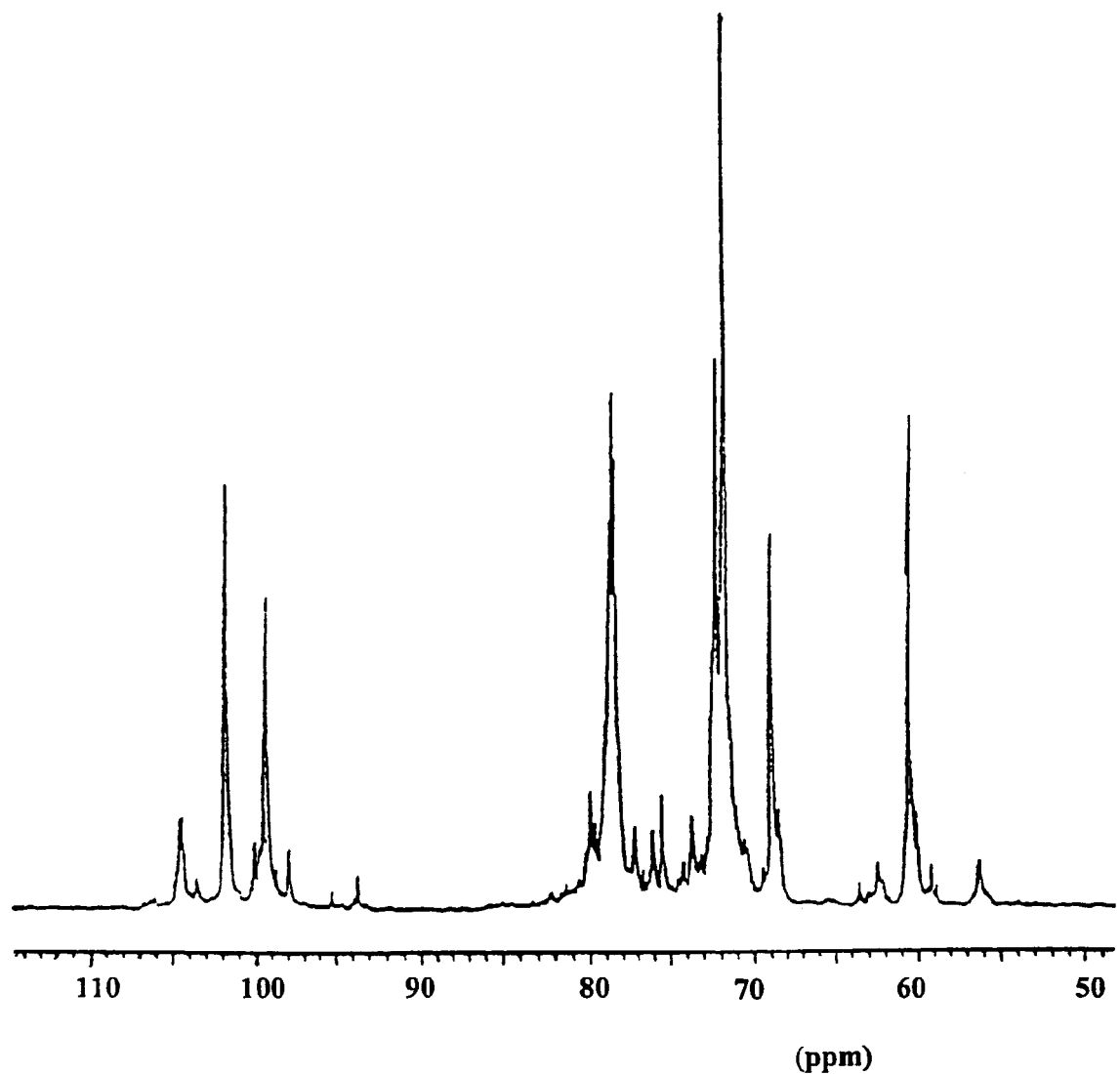
FIG. 2 represents the NMR test of the glycosaminoglycan having an average molecular weight of 2,400 (±200) as obtained by the described example.

| CHEMICO-PHYSICAL CHARACTERISTICS | |
|---|---|
| Appearance: | light yellow colour powder |
| Average molecular weight: | 2,400 D (±200) |
| Molecular weights distribution: | 95% <2,560 D −>1,920 D |
| Polydispersion index: | '11.20 |
| Organic sulphur: | 9.5–11.5% |
| SO3/COOH ratio: | 2.3–2.6 |
| Specific rotation: | >+35° |
| HPLC: | FIG. 1 |
| NMR: | FIG. 2 |

The average molecular weight has been determined by HPLC using columns for exclusion chromatography, in comparison with LMW Heparins for Calibration Reference Substance Batch no. 1a (PH.EUR.) at molecular weight =3,700.

Sulphation Percent Ratios

Three samples have been examined with the results of Table 1.

TABLE NO. 1

| Desulfated Uronic Acids % | GlcNSO$_3$.6SO$_3$ % | GlcNAc % | GlcNSO$_3$.3,6SO$_3$ % |
|---|---|---|---|
| 34 | 85 | 13 | 7 |
| 33 | 85 | 13 | 6 |
| 31 | 85 | 14 | 7 |

The percent values are computed on the sum of two specific areas taken into consideration from the NMR analysis.

Desulfated uronic acids: area of the signals 102.2 and 106 ppm with respect to the total uronic acids at 100.5 and 106 ppm;

Glucosamine.NSO$_3$-6-sulfated: area of the signals at 62.5 ppm with respect to the area of the Glucosamine-6-sulfated at 68 ppm;

Glucosamine.N acetilated: area of the signals at 55.5 ppm with respect to the area of the signals from 61 to 54 ppm;

Glucosamine.N,3 sulfated: area of the signal at 59 ppm with respect to the area of the signals from 61 to 54 ppm.

The values of the sulfation in C.6 of the glucosamine turn out to be lower than the ones of the fractions having 4,500 D (84 average) molecular weight.

This is due to the fact that, with the lowering of the molecular weight, the secondary alcoholic groups present in the reduced terminal units whose signals fall into the zone of the C6 of the Glucosamines 6 desulfated increase.

Structural Characteristics

The FIG. 1 reports the plot obtained by HPLC of the fraction of glycosaminoglycans with the distribution of the molecular weights ranging for 95% from 2,560 D to 1,920 D, corresponding to about 4–5 constitutive Disaccharides. The FIG. 2 reports the NMR plot of the same fraction wherein one notices the absence of signals from 84 to 85 ppm characteristic of the linkage site which is removed by depolymerization with gamma radiation. The detachment of the galactosidic chain and its nitrogenous components represents a specific characteristic of this saccharidic fraction allowing to operate without the interferences, usually of pathological character, deriving from the presence of peptidic structures having different aminoacidic composition.

The NMR analysis reveals moreover that in the terminal zones there are only intact rings or eventually consisting of aliphatic "remnants".

The rings of the reducing end are never desulfated.

Glucuronic structures desulfated at the reducing ends are not pointed out because they are destroyed by the gamma radiation.

In the rings of the not reducing ends the terminal C4s are difficult to distinguish from the not terminal C4s because they all fall into the same zone; the only ones which are identified in an univocal way are those ones of the NS, 3S glucosamine exactly adjacent to the glucuronic acid of the active pentamer.

The structural cores correspond to the initial heparin with practically unaltered sulfation indexes.

The anomeric signals deriving from the $GlcNSO_{36}SO_3$ and $IdoA2SO_3$ reducing groups qualify the fraction of glycosaminoglycans according to the invention as a substance with terminal units similar to those of the fragments from natural heparin.

Particularly suitable for the use according to the present invention is the fraction of glycosaminoglycans having an average molecular weight of 2,400 D with polydispersion index lower than 1.20, with total absence of peptidic components and free from desulfated units at the reducing end, obtained without resulfation treatment and in the absence of catalyzers.

Biological Characteristics

Ph.E. heparinic activity=absent
USP heparinic activity=absent
Anti Xa activity=<50 U aXa/mg
Anti IIa activity=<10 U aIIa/mg From the above reported characterization it turns out that the fraction of glycosaminoglycans according to the present invention proves the absence of an heparinic activity towards the parameters of the coagulation notwithstanding the maintenance of the structural characteristics of the heparinic molecule, obviously with much lower molecular weight of the heparin.

EXAMPLE 100 g of sodium Heparin from pig intestinal mucosa, having a molecular weight of 14,000 D and an activity of 190 U/mg, are dissolved in 1 l of distilled and de-aerated water. The solution is poured into pyrex containers which are closed with a glass plug after bubbling of Argon.

The solution is submitted to an overall treatment of 130 kGy at subsequent dosages of about 25 kGy of gamma radiation from Co 60, obtaining the depolymerization of the Heparin.

The irradiated solution is ultrafiltered at 300 D cut-off, purified with subsequent passages in 3% NaCl and freeze-dried, after concentration at about 10%. This "mother depolymerized" Heparin is dissolved at 10% in 0.3 M solution of NaCl and fractioned by Gel Permeation column containing Sephadex G 50 Medium.

After separating the components having molecular weight >8,000 D and the aliquots referable to the Heparin of about 4,500 D, the fractions at a molecular weight <3,000 D are recovered.

These fractions are purified by 600 D cut-off ultrafiltration for the removal of the molecular fragments following the depolymerization process.

After a series of three washings in 0.3 M NaCl to obtain the disappearance of the reaction to the carbazole in permeate, the mixture is concentrated to about 8% and the solution passed by 0.2 micrometers filtration is freeze-dried.

The freeze-dried product is dissolved in a solution of 0.3 M NaCl in an amount such as to obtain a final concentration of 10% (x/v). This solution is fractioned by Gel Permeation on column containing Sephadex G/25 medium.

The fractions having molecular weight ranging from 1,920 D to 2,560 D are gathered.

The obtained solution is purified by 300 D cutoff ultrafiltration to the elimination of the sodium chloride.

The solution is concentrated at about 10% and freeze-dried.

Yield: about 9 g of light yellow colour powder.

Analysis: average molecular weight=2,400 (±200); organic sulphur=9.9%.

Sulfates/carboxyls ratio=2.5; anti Xa activity=45 U anti Xa/mg.

HPLC test, FIG. 1.

NMR test, FIG. 2.

For comparison aim, with the same method also the following fractions of glycosaminoglycans are prepared:

Fraction having average molecular weight of 640 D (from 320 to 1,600 D);

Fraction having average molecular weight of 4,800 D (from 3,350 to 6,060 D).

Thanks to the pharmaceutical characteristics resulting from the experimentation reported below, the glycosaminoglycans having average molecular weight equal to 2,400 D may be used for the preparation of pharmaceutical compositions suitable for the treatment of senile dementia, and in particular of the Alzheimer's disease or SDAT (Senile Dementia Alzheimer's Type), and of the cerebral neurological lesions from ictus and from traumas and of the forms of nervous degeneration.

The compositions comprise a pharmaceutically effective amount of the glycosaminoglycans in a mixture with pharmaceutically acceptable diluents or excipients, and they may be prepared in a form suitable for the subcutaneous, intramuscular, intravenous and oral administration.

The compositions contain an amount of the glycosaminoglycans ranging from 50 to 200 mg per unitary dose.

The present invention also includes a therapeutic method for the treatment of patients suffering from senile dementia, and in particular from Alzheimer's disease or SDAT and from cerebral neurological lesions from ictus and from traumas, consisting in the administration of an amount of glycosaminoglycans having an average molecular weight of 2,400 D ranging from 10 to 400 mg per day. In particular, for the subcutaneous, intramuscular and intravenous administration is expected an amount from 10 to 200 mg per day and for the oral administration an amount from 25 to 400 mg per day is expected.

Pharmacological Experimentation

For the study of the pharmacological activity of the fraction of glycosaminoglycans according to the present invention an experimental model has been applied in rat reproducing some of the lesions tipycal of senile dementia (Sigurdsson E M; Lorens S A; Hejna M J; Dong W X; Lee J M. "Local and Distal Histopathological Effects of Unilateral Amyloid-β 25–35 Injections into the Amygdala of Young F344 Rats". Neuro Biol Aging 1996; 17:893–901).

In particular the following parameters have been studied:

Tau-2 protein, correlated to the entity of the reaction to the β amyloid substance (indirect reactivity);

GFAP protein (glial fibrillary acid protein), correlated to the reactivity of the astrocytes to the β amyloid (direct reactivity).

Materials Used in the Experimentation

β amyloid:

Aβ 25–35 sodium salt in a solution of trifluoroacetic acid (TFA) (VEH1) with a peptide content of 82–89% (BACHEM, Torrance, Calif.).

The β amyloid with the respective vehicle (VEH 1) was diluted with Nanopure $H_2O$ in an amount such as to obtain a concentration of 5 nmol/3.0 ml, immediately before the use and maintained at 4° C.

Glycosaminoglycans, TGSS:

three types of TGSS (tailored glycosaminoglycans) have been used prepared as described above and having different molecular weight as from the following Table:

| Kind of TGSS | Average molecular weight (D) | Average number of monosaccharides |
|---|---|---|
| C8 | 640 (320–1600) | 2 |
| C3 | 2400 (1920–2560) | 8 |
| C7 | 4800 (3520–6060) | 15 |

These products consisted of a powder of light yellow colour soluble in water, which was conserved in a drier at room temperature.

For the injection in rats solutions at the concentration of 1 mg/ml in physiological solution (VEH2) were prepared.

The solutions were maintained at the temperature of 4° C. for a period not longer than two weeks.

VEH 1:

Trifluoroacetic acid (TFA) (10 nmoles in 3μ liters of distilled $H_2O$), vehicle of the β amyloid.

VEH2:

Physiological solution, vehicle of the TGSS.

Experimentation Methods

The model used for the experimentation is based on the effects of an injection of Aβ 25–35 in the centro-cerebral region of the amygdala.

The aminoacidic sequence of Aβ 25–35 is the sequence considered neurotoxic (Yankner B A; Duffy L K; Kirscner D A; "Neurotrophic and Neurotoxic Effects of Amyloid-β Protein. Reversal by Tachykinin Neuropeptides". Science 1990: 250–282) as it produces the lesions tipical of Aβ 1–41 or Aβ 1–43.

For the experiments young (3–4 months) male rats have been used, of Fischer 344 strain, which received an intracerebral injection in the right amygdala with 5 nmol/3.0 μl of Aβ 25–35 or the respective vehicle (VEH 1).

The TGSS or the respective VEH2 vehicle were administered 2 times per day by subcutaneous way from two days before the intracerebral injection of Aβ and for 32 days after said injection, with the doses specified below.

For the histological analysis the animals were anaesthetized with pentobarbital sodium and perfused by arterial (transaortic) way with a solution of 4% formaldehyde.

5 coronal sections (40 μm) were carried out spaced with 0.2 mm intervals.

The sections were contacted with antibodies for the Tau-2 protein and for the glial fibrillary acid protein (GFAP).

The Fischer 344 rats were obtained from Harlan Sprague-Dawley Inc. (Indianapolis Ind.).

At the arrival time they weighed 250–300 g and they were from 3 to 4 months old. The animals were kept in individual cages with a light-darkness cycle equal to 12 hours (light at 7.00 am) in conditions of housing approved according to the AAALAC (American Association Animal Laboratory and Care).

They had access to food and water ad libitum and they have been kept in these environmental conditions for 2–3 weeks before the experiment.

The intracerebral injection of Aβ 25–35 was done under anaesthesia with pentobarbital sodium (50 mg/kg, i.p.; Butler, Columbus, Ohio).

On the anaesthetization of the animals, atropine sulfate (0.4 mg/kg; Sigma, St. Louis, Mo.) and ampicillin sodium salt (50 mg/kg; Sigma, St. Louis, Mo.) were also administered by intramuscular way. The intracerebral injection into the right amygdala was carried out by the use of a stereotaxic (Kopf) instrument set such a way that the depth was not greater than 3.3 mm under the interaural line.

The coordinates for the injection have been determined on the basis of the Paxinos and Watson atlas measured from the cranial bregma with coordinates AP-3.0, ML4.6 and DV-8.8.

The anteroposterior (AP) coordinates have been positioned where the structure of the amygdala is wider.

The medium lateral (ML) coordinates have been centred in relation to the medial and basolateral core of the amygdala and finally the dorsoventral (DV) coordinates have been centred at the dorsoventral limina of the amygdala. The injected volume of 3 μl has been infused in 6 minutes, using a pump for microsyringes of CMA/100 kind (Carnegie Medici AD, Soin, Sweden). The cannula remained in situ for 2 minutes after the injection and then it has been carefully removed.

After the operation the animals stood on a heated plate till the moment when they reacquired the righting reflex.

After 35 days of treatment the animals were anaesthetized with pentobarbital sodium (100 mg/kg I.P.) and perfused by transaortic way with 250 ml of a sodium/potassium phosphate 0.1 M buffer at pH 7.4 (PB).

Subsequently formaldehyde at 4% was perfused in 500 ml of PB, at the velocity of 500 ml/hour at room temperature.

Immediately after the beginning of the perfusion 1 U/g of heparin (Upjohn Kalamzoo. Mich.) were injected by transaortic way.

After the perfusion the brain was isolated and fixed with a solution at 20% of sucrose for 1 h and then it was sectioned in 6 mm blocks around the injection site and kept at a temperature of 4° C. in a 20% sucrose and 0.1% sodium azide solution and at 0.01% of bacitracin in PB for 24 hours.

The tissue blocks were on end transferred into a solution at 20% of glycerol and at 2% of dimethyl sulfoxide in 0.1 M sodium phosphate buffer and therein kept, at a temperature of 4° C., till the moment of the section.

The coronal sections of 40 μm were cut in series of 5 at a distance of 0.2 mm one from another and histologically analyzed for the analysis of the Tau-2 and GFAP proteins.

Histological Analysis

Cresyl violet

The sections were cleaned with xylene and hydrated with alcohol and $H_2O$. The coloration was carried out putting the section in contact with a solution containing 200 ml of 0.2 M acetic acid, 133 ml of 0.2 M sodium acetate and 67 ml of cresyl violet acetate at 0.1%. Then the sections were dehydrated with subsequent passages in ethanol and cleaned with xylene. The thus colored section was covered with suitable slide for the microscope reading.

Congo Red

The sections were cleaned and hydrated with a series of treatments with ethanol and water.

The coloration was carried out putting into contact the section with a solution containing 1% of Congo Red and 50% of ethanol for a period of 1 h.

Then the sections were dipped into a solution saturated with lithium carbonate and washed under running water for 15 minutes. The counter-coloration was carried out in Harris hematoxylin for 2 minutes and later on water and a 1% alcoholic acid solution were added. The sections were washed in water, dipped into an aqueous solution of ammonium sulfate and again washed with running water. The sections were finally dehydrated in ethanol and cleaned with xylene. The so coloured sections were covered with a suitable slide for the reading at the microscope.

Tau-2 Protein

The 40 μm sections were cleaned from the cryoprotector and kept overnight in PBS buffer solution at 4° C.

In the morning the sections were put into contact for 30 minutes with a 0.3% solution of $H_2O_2$ in tris buffer solution at pH 7.6 (PBS) and later on washed 3 times for 10 minutes with a solution at 0.3% of triton X-100 in PBS. The sections were then incubated for 24 hours with Tau-2 (Sigma) antibody 1:500 diluted at room temperature.

The diluent for antibody contained 2% of triton X-100, 0.1% of sodium azide, 0.01% of bacitracin, 2% of seric albumin and 10% of normal horse serum in PBS. On end the tissue was washed 3 times, for 10 minutes, with a solution containing 0.3% of triton X-100 in PBS and subsequently incubated for 1 h with an antibody for immunoglobulin (Vectastain ABC Elite Kit, Vector Laboratories Burlingame Calif.) diluted 1:200 in a solution at 0.3% of triton X-100 in PBS. After 2 washings with a solution at 0.3% of triton X-100 in PBS, for a 15 minutes total, the tissue was incubated for 1 h with horseradish avidin peroxidase (Vector) diluted 1:2,000 with a solution at 0.3% of triton X-100 in PBS.

The sections were then washed in PBS for 1 hour and then again for 15 minutes with a sodium acetate buffer (0.2 M at pH 6.0). The sections were then reacted with 3-3 diaminobenzidine tetrahydrochloride (DAB) and with nickel ammonium sulphate (35 mg of DAB, 2.5 g of ammonium nickel sulphate for 100 ml of sodium acetate buffer with 0.3% of $H_2O_2$).

The sections were then put in sodium acetate buffer and subsequently in PBS at 4° C. and therein maintained overnight.

After this operation the sections were dried and covered with a slide for the reading at the microscope.

GFAP Protein

The coloration has been done by the method used for the Tau-2 with the exception that the antibody was diluted in sheep serum rather than in horse serum.

The GFAP (DAKO, Denmark) primary antibody was used in 1:500 dilution.

The sections coloured with cresyl violet were analyzed measuring the sizes of the Aβ deposits.

The area of the Aβ deposits was measured at 0.2 mm intervals. The Aβ deposits were also analyzed for the apple green refractivity, using the polarized light of the slides coloured with Congo red.

In the context of these histochemical showings the cells reactive to Tau-2 were counted in all the coronal sections while the reactive astrocytosis was estimated, with a score from 0 to 2.

The animals were considered positive if they exhibited positive colorations from 1 to 2.

Experimental Procedure and Results

For each experiment four different groups of rats have been used:

1. VEH1+VEH2 GROUP: rats injected with the VEH1 (TFA) vehicle in the amygdala and injected with the VEH2 (physiological solution) vehicle by subcutaneous way;
2. Aβ+VEH2 GROUP: rats injected with Aβ 25–35 in the amygdala and with the VEH2 (physiological solution) vehicle by subcutaneous way;
3. Aβ+TGSS GROUP: rats injected with Aβ 25–35 in the amygdala and TGSS by subcutaneous way;
4. VEH1+TGSS GROUP: rats injected with the VEH1 (TFA) vehicle in the amygdala and with a TGSS by subcutaneous way.

Each block of experiments was designed for at least 6 animals per group.

Following this treatment scheme three types of TGSS have been used with three different average molecular weights as follows:

C3-2,400 Dalton, at 2.5 mg/kg s.c. dose
C8-640 Dalton, at 2.5 mg/kg s.c. dose
C7-4,800 Dalton, at 2.5 mg/kg s.c. dose.

Each TGSS has been studied with two different experiments to have the confirmation of the results.

For each type of treatment the following number of animals has been analyzed:

| TREATMENTS | | NUMBER OF ANIMALS |
|---|---|---|
| 1. | VEH1 + VEH2 | 30 |
| 2. | Aβ + VEH2 | 36 |
| 3a. | Aβ + C3 | 23 |
| 3b. | Aβ + C8 | 17 |
| 3c. | Aβ + C7 | 21 |
| 4. | VEH1 + TGSS (C3 or C7 or C8) | 30 |

The animals treated with VEH1 intra amygdala (controls without amyloid) and with one whatever of the TGSS(C3 or C8 or C7) have always showed results practically identical to the controls of the group 1, treated with the only VEH1+VEH2 vehicles.

a) Reactivity to the Tau-2 protein (number of reactive cells): average values ± standard deviation.

| TREATMENTS | Number of Cases | Number of Reactive Cells/ Tissue Section |
|---|---|---|
| 1. VEH1 + VEH2 | 30 | 11 ± 5 |
| 2. Aβ + VEH2 | 36 | 66 ± 12 |
| 3a. Aβ + C3 | 23 | 25 ± 16 p < 0.05 Vs Aβ + VEH2 (Newman-Keuls test) |
| 3b. Aβ + C8 | 17 | 60 ± 14 |
| 3c. Aβ + C7 | 21 | 22 ± 17 p < 0.05 Vs Aβ + VEH2 (Newman-Keuls test) |
| 4. VEH1 + TGSS (C3 or C7 or C8) | 30 | 10 ± 3 |

From this series of experiments turns out that C3 and C7 are both active in reducing the reactivity to the Tau-2 protein while C8 which has the lowest molecular weight, corresponding to the disaccharide, shows no activity.

The controls not treated with Aβ behave in an identical way when they are injected by subcutaneous way either with physiological solution (group 1) or with a TGSS (group 4).

The strong decrease of the reactivity to the Tau-2 protein through the effect of the C3 compound has been confirmed also by tests wherein the C3 has been administered to the rats by oral way.

The experimental model and the screaning methodology have been identical to those ones above described, with the difference that the C3 has been administered by oral way at a dose of 20 mg/kg rather than subcutaneous way.

The C3 administration has been carried out one time a day starting from three days before the injection of the Aβ 25–35 to fourteen days after such injection. The rats were sacrificed after fourteen days from the injection of the Aβ 25–35.

The obtained results are reported in the following Table from which one observes that C3 strongly reduces the reactivity to the Tau-2 protein in the rats treated with Aβ 25–35.

| TREATMENTS | NUMBER OF CASES | NUMBER OF REACTIVE CELLS/TISSUE SECTION |
|---|---|---|
| Aβ + VEH2 | 6 | 52 ± 7 |
| Aβ + C3 | 6 | 9 ± 2 p < 0.01 (Student T test) | b) Reactivity of the astrocytes (% of animals which represented reactivity +1 or +2): average values.

| TREATMENTS | Number of Cases | % of animals which represented reactivity +1 or +2 |
|---|---|---|
| 1. VEH1 + VEH2 | 30 | 37 |
| 2. Aβ + VEH2 | 36 | 87 |
| 3a. Aβ + C3 | 23 | 35 p < 0.05 Vs Aβ + VEH2 ($\chi_2$ sec. Fisher) |
| 3b. Aβ + C8 | 17 | 88 |
| 3c. Aβ + C7 | 21 | 67 |
| 4. VEH1 + TGSS (C3 or C7 or C8) | 30 | 26 |

As tar as the astrocytes reactivity is concerned the only product which shows a significant activity is C3 (group 3a). The products C8 and C7 (groups 3b and 3c) have no activity.

From the examination of these results surprisingly emerges that the C3 TGSS, having an average molecular weight of equal to 2,400 D, has a much higher activity than the TGSS which respectively have higher and lower molecular weights. In particulars the average molecular weight equal to 2,400 Dalton is optimal for the reduction of the reactivity pointed out with the Tau-2 protein and for that one pointed out with the reaction of the astrocytes.

In another experimentation on rats the capacity of the C3 product to overcome the hematoencephalic barrier following the administration by intravenous way has been studied.

For that purpose the product marked with tritium ($^3$H) has been used.

The labeling corresponded to 700,000 DPM/mg of $^3$H-C3.

After a 2.5 mg/kg administration by intravenous way, the rats have been sacrificed, under anaesthesia by pentobarbital sodium, at the fixed time of 45 minutes.

The labeling levels in blood, in the cerebrospinal fluid (CSF) and finally in the brain (after a slow infusion to remove the blood from the vessels) have been analyzed. The CSF has been taken with a glass capillary from the fourth ventricle (in an amount always greater than 200 µl, after complete bleeding of the animal).

The DPM have been estimated through scintillation diluting 20 µl of homogenate (brain) in 5 ml of physiological solution.

The results, reported in the following table, show that $^3$H—C3 is able to pass the hematoencephalic barrier in a significant amount.

| TISSUE | NUMBER OF CASES | DPM/ml |
|---|---|---|
| Serum | 5 | 404 ± 138.3 |
| CSF | 5 | 85 ± 13.0 |
| Brain | 5 | 217 ± 217.2 |

In the control animals the DPM/ml values were always lower than 41 in all the analyzed tissues.

Following on these results a control of the presence of the anti Xa activity in serum, in CSF and in the brain has been carried out.

It is known that the Xa factor (coagulation X factor) is inhibited only by the sulphur oligosaccharidic fractions containing more than four saccharides.

In a series of rats treated as in the previous point, it has been observed that, after 45 minutes since the treatment with C3 at a dose of 2.5 mg/kg by intravenous way, the anti Xa activity is present in a significant way in plasma, in CSF and in the cerebral tissue.

This is a further confirmation that the product passing the hematoencephalic barrier consists of C3 and not of inactive degradation products such as the disaccharides or the tetrasaccharides.

In the rats submitted to injection of Aβ 25–35 either treated with C3 or without active treatments the neuronal growth has been analyzed too.

For the purpose the Rapid Golgi coloration method has been used which, owing to its complexity, has been applied only to a limited number of animals.

As already previously specified the C3 has been administered at a dose of 2.5 mg/kg by subcutaneous way, twice a day starting from two days before the intracerebral injection of Aβ 25–35 and for 32 consecutive days.

The cerebral neurones of the V layer of the cingulate gyrus of the brain have been analyzed.

The test implied the measurement of the dendrites length and the ratio between the number of end branches and the number of the primitive branches (T/B ratio). The higher the T/B ratio the greater is the complexity and the number of connections of the neuron.

The results are reported in the following Table.

| Treatments | Number of cases | Dendrites length % | T/B ratio |
|---|---|---|---|
| VEH1 + VEH2 | 7 | 100 ± 2.1 | 4.3 ± 0.15 |
| Aβ + VEH2 | 8 | 94 ± 2.0 | 4.0 ± 0.16* |
| Aβ + C3 | 6 | 110 ± 3.0 | 4.7 ± 0.19** |

*$p < 0.05$ Aβ + VEH2 Vs VEH1 + VEH2
**$p < 0.05$ Aβ + VEH2 Vs Aβ + C3

The Table shows that the AP creates a damage to the neuronal growth and that the C3 remedies the created damage. Moreover one notices that C3 has a neurotrophic kind activity useful in case of nervous degeneration or traumas implying a neuronal damage.

What is claimed is:

1. A therapeutic method for the treatment of a subject having senile dementia or neurological cerebral lesions from ictus and traumas, comprising administering to said subject in need thereof a therapeutically effective amount of glycosaminoglycans having an average molecular weight of 2,400 D +/−200 D obtained by depolymerization of heparin.

2. The therapeutic method according to claim 1, wherein said senile dementia is Alzheimer's disease or SDAT (Senile Dementia Alzheimer's Type).

3. The therapeutic method according to claim 1, wherein said glycosaminoglycans have a polydispersion index of less than 1.20, and are free from peptidic components and desulfated units at the reducing end.

4. The therapeutic method according to claim 1 wherein said glycosaminoglycans are administered in a dosage of from 10 to 400 mg per day.

5. The therapeutic method according to claim 4, wherein said glycosaminoglycans are administered by oral route in a dosage of from 25 to 400 mg per day.

6. The therapeutic method according to claim 4, wherein said glycosaminoglycans are intravenously or intramuscularly administered in a dosage of from 10 to 200 mg per day.

* * * * *